(12) United States Patent
Roe et al.

(10) Patent No.: US 8,974,432 B2
(45) Date of Patent: Mar. 10, 2015

(54) OUTER COVER FOR AN ABSORBENT ARTICLE

(75) Inventors: Donald Carroll Roe, West Chester, OH (US); Elaine Mary Wiggins, Fairfield Township, OH (US)

(73) Assignee: The Procter & Gamble Company, Cincinnati, OH (US)

(*) Notice: Subject to any disclaimer, the term of this patent is extended or adjusted under 35 U.S.C. 154(b) by 317 days.

(21) Appl. No.: 13/188,492

(22) Filed: Jul. 22, 2011

(65) Prior Publication Data

US 2012/0022481 A1    Jan. 26, 2012

Related U.S. Application Data

(60) Provisional application No. 61/366,670, filed on Jul. 22, 2010, provisional application No. 61/484,782, filed on May 11, 2011.

(51) Int. Cl.
| | |
|---|---|
| *A61F 13/505* | (2006.01) |
| *A61F 13/68* | (2006.01) |
| *A61F 13/74* | (2006.01) |
| *A61F 13/49* | (2006.01) |
| *A61F 13/15* | (2006.01) |
| *A61F 13/51* | (2006.01) |
| *A61F 13/514* | (2006.01) |

(52) U.S. Cl.
CPC ......... *A61F 13/49004* (2013.01); *A61F 13/505* (2013.01); *A61F 2013/15284* (2013.01); *A61F 2013/15471* (2013.01); *A61F 2013/15512* (2013.01); *A61F 2013/5055* (2013.01); *A61F 2013/5103* (2013.01); *A61F 2013/51033* (2013.01); *A61F 2013/5145* (2013.01)

USPC ............... 604/397; 604/385.14; 604/374

(58) Field of Classification Search
USPC ............ 604/378, 381, 374, 385.14, 385.15, 604/393–399
See application file for complete search history.

(56) References Cited

U.S. PATENT DOCUMENTS

| 2,530,647 A | 11/1950 | Buehler |
| 2,688,328 A | 9/1954 | Marcus |
| 2,793,642 A | 5/1957 | Andruhovici |
| 3,077,193 A | 2/1963 | Mann |
| 3,162,196 A * | 12/1964 | Salk ............................ 604/399 |

(Continued)

FOREIGN PATENT DOCUMENTS

| AU | 642 386 | 10/1993 |
| CA | 2 103 537 | 2/1995 |

(Continued)

OTHER PUBLICATIONS

PCT International Search Report dated Dec. 22, 2011, 10 pages.

(Continued)

*Primary Examiner* — Tan-Uyen (Jackie) T Ho
*Assistant Examiner* — Kathryn E Ditmer
(74) *Attorney, Agent, or Firm* — Sarah M. DeCristofaro; Abbey A. Lopez; Amy M. Foust

(57) ABSTRACT

An outer cover for an absorbent article has an absorbent capacity in addition to the absorbency of an absorbent insert. The outer cover may have two or more layers, at least one of which has liquid absorption capacity. Another layer may be hydrophobic. The outer cover as a whole may be breathable and water-impermeable.

19 Claims, 4 Drawing Sheets

(56) References Cited

U.S. PATENT DOCUMENTS

| | | |
|---|---|---|
| 3,496,259 A | 2/1970 | Guenther |
| 3,560,292 A | 2/1971 | Butter |
| 3,574,791 A | 4/1971 | Patsy et al. |
| 3,719,736 A | 3/1973 | Woodruff |
| 3,735,424 A | 5/1973 | Maggio et al. |
| 3,860,003 A | 1/1975 | Buell |
| 3,911,173 A | 10/1975 | Sprague, Jr. |
| 3,926,189 A | 12/1975 | Taylor |
| 3,929,135 A | 12/1975 | Thompson |
| 3,955,575 A | 5/1976 | Okuda |
| 4,022,210 A | 5/1977 | Glassman |
| 4,072,150 A | 2/1978 | Glassman |
| 4,081,301 A | 3/1978 | Buell |
| 4,116,892 A | 9/1978 | Schwarz |
| 4,223,059 A | 9/1980 | Schwarz |
| 4,265,245 A | 5/1981 | Glassman |
| 4,284,454 A | 8/1981 | Joa |
| 4,324,246 A | 4/1982 | Mullane et al. |
| 4,326,302 A | 4/1982 | Lowe et al. |
| 4,338,939 A | 7/1982 | Daville |
| 4,342,314 A | 8/1982 | Radel et al. |
| 4,352,356 A | 10/1982 | Tong |
| 4,397,646 A | 8/1983 | Daniels et al. |
| 4,438,167 A | 3/1984 | Schwarz |
| 4,463,045 A | 7/1984 | Ahr et al. |
| 4,475,912 A | 10/1984 | Coates |
| 4,496,360 A | 1/1985 | Joffe et al. |
| 4,573,986 A | 3/1986 | Minetola et al. |
| 4,578,073 A | 3/1986 | Dysart et al. |
| 4,579,556 A | 4/1986 | Mcfarland |
| 4,582,550 A | 4/1986 | Sigl |
| 4,597,760 A | 7/1986 | Buell |
| 4,597,761 A | 7/1986 | Buell |
| 4,609,518 A | 9/1986 | Curro et al. |
| 4,610,678 A | 9/1986 | Weisman et al. |
| 4,615,695 A | 10/1986 | Cooper |
| 4,629,643 A | 12/1986 | Curro et al. |
| 4,643,726 A | 2/1987 | Gegelys |
| 4,650,483 A | 3/1987 | Joffe |
| 4,657,539 A | 4/1987 | Hasse |
| 4,661,102 A | 4/1987 | Shikata et al. |
| 4,673,402 A | 6/1987 | Weisman et al. |
| 4,695,278 A | 9/1987 | Lawson |
| 4,701,170 A | 10/1987 | Wilson et al. |
| 4,704,114 A | 11/1987 | Wilson et al. |
| 4,710,187 A | 12/1987 | Boland et al. |
| 4,743,239 A * | 5/1988 | Cole ................. 604/385.23 |
| 4,747,846 A | 5/1988 | Boland et al. |
| 4,756,709 A | 7/1988 | Stevens |
| 4,770,656 A | 9/1988 | Proxmire et al. |
| 4,773,906 A | 9/1988 | Krushel |
| 4,785,996 A | 11/1988 | Ziecker et al. |
| 4,795,452 A | 1/1989 | Blaney et al. |
| 4,795,454 A | 1/1989 | Dragoo |
| 4,808,176 A | 2/1989 | Kielpikowski |
| 4,808,177 A | 2/1989 | Desmarais et al. |
| 4,808,178 A | 2/1989 | Aziz et al. |
| 4,816,026 A | 3/1989 | Richardson |
| 4,821,342 A * | 4/1989 | Troyer ................. 2/82 |
| 4,834,735 A | 5/1989 | Alemany et al. |
| 4,834,736 A | 5/1989 | Boland et al. |
| 4,834,737 A | 5/1989 | Khan |
| 4,834,738 A | 5/1989 | Kielpikowski et al. |
| 4,842,666 A | 6/1989 | Werenicz |
| 4,872,871 A | 10/1989 | Proxmire et al. |
| 4,880,423 A * | 11/1989 | Green ................. 604/391 |
| 4,888,231 A | 12/1989 | Angstadt |
| 4,892,536 A | 1/1990 | Desmarais et al. |
| 4,892,598 A | 1/1990 | Stevens et al. |
| 4,906,243 A | 3/1990 | Dravland |
| 4,908,247 A | 3/1990 | Baird et al. |
| 4,909,803 A | 3/1990 | Aziz et al. |
| 4,936,840 A | 6/1990 | Proxmire |
| 4,955,880 A | 9/1990 | Rodriquez |
| 4,961,736 A | 10/1990 | McCloud |
| 4,961,737 A | 10/1990 | Orlando et al. |
| 4,964,857 A | 10/1990 | Osborn |
| 4,968,311 A | 11/1990 | Chickering et al. |
| 4,968,312 A | 11/1990 | Khan |
| 4,978,046 A | 12/1990 | Hagmann et al. |
| 4,981,480 A | 1/1991 | Gaudet et al. |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,019,068 A | 5/1991 | Perez et al. |
| 5,021,051 A | 6/1991 | Hiuke |
| 5,032,120 A | 7/1991 | Freeland et al. |
| 5,037,416 A | 8/1991 | Allen et al. |
| 5,069,672 A | 12/1991 | Wippler et al. |
| 5,087,253 A | 2/1992 | Cooper |
| 5,108,385 A | 4/1992 | Snyder |
| 5,127,108 A | 7/1992 | Weiss |
| 5,137,537 A | 8/1992 | Herron et al. |
| 5,141,870 A | 8/1992 | Bedbrook et al. |
| 5,147,345 A | 9/1992 | Young et al. |
| 5,155,867 A * | 10/1992 | Norvell ................. 2/113 |
| 5,156,793 A | 10/1992 | Buell et al. |
| 5,167,897 A | 12/1992 | Weber et al. |
| 5,185,011 A | 2/1993 | Strasser |
| 5,202,173 A | 4/1993 | Wu et al. |
| 5,207,663 A | 5/1993 | McQueen |
| 5,210,882 A | 5/1993 | Moretz et al. |
| 5,217,447 A | 6/1993 | Gagnon |
| 5,234,423 A | 8/1993 | Alemany et al. |
| 5,254,111 A | 10/1993 | Cancio et al. |
| 5,260,345 A | 11/1993 | Desmarais et al. |
| 5,261,901 A * | 11/1993 | Guay ................. 604/391 |
| 5,269,775 A | 12/1993 | Freeland et al. |
| 5,291,617 A * | 3/1994 | Moretz et al. ................. 2/400 |
| 5,296,184 A | 3/1994 | Wu et al. |
| 5,306,267 A | 4/1994 | Hahn et al. |
| 5,342,338 A | 8/1994 | Roe |
| 5,354,597 A | 10/1994 | Capik et al. |
| 5,360,422 A | 11/1994 | Brownlee et al. |
| 5,368,584 A | 11/1994 | Clear et al. |
| 5,368,585 A | 11/1994 | Dokken |
| 5,387,207 A | 2/1995 | Dyer et al. |
| 5,401,266 A | 3/1995 | Runeman et al. |
| 5,405,342 A | 4/1995 | Roessler et al. |
| 5,415,650 A | 5/1995 | Sigl |
| 5,435,014 A | 7/1995 | Moretz et al. |
| 5,458,591 A | 10/1995 | Roessler et al. |
| 5,476,457 A | 12/1995 | Roessler et al. |
| 5,514,121 A | 5/1996 | Roe et al. |
| 5,518,801 A | 5/1996 | Chappell et al. |
| 5,554,142 A | 9/1996 | Dreier et al. |
| 5,562,648 A * | 10/1996 | Peterson ................. 604/370 |
| 5,571,096 A | 11/1996 | Dobrin et al. |
| 5,607,760 A | 3/1997 | Roe |
| 5,609,587 A | 3/1997 | Roe |
| 5,613,959 A | 3/1997 | Roessler et al. |
| 5,624,425 A | 4/1997 | Gray et al. |
| 5,625,222 A | 4/1997 | Yoneda et al. |
| 5,635,191 A | 6/1997 | Roe et al. |
| H1670 H | 7/1997 | Aziz et al. |
| 5,643,588 A | 7/1997 | Roe et al. |
| 5,667,503 A | 9/1997 | Roe et al. |
| 5,671,615 A | 9/1997 | Kj.ae butted.rgaard et al. |
| 5,716,349 A | 2/1998 | Taylor et al. |
| H1732 H | 6/1998 | Johnson |
| 5,769,838 A | 6/1998 | Buell et al. |
| 5,772,649 A | 6/1998 | Siudzinski |
| 5,776,121 A | 7/1998 | Roe et al. |
| 5,795,347 A | 8/1998 | Roe et al. |
| 5,795,348 A | 8/1998 | Roe et al. |
| 5,807,371 A | 9/1998 | Toyoda et al. |
| 5,814,037 A | 9/1998 | Coates |
| 5,827,261 A | 10/1998 | Osborn et al. |
| 5,843,065 A | 12/1998 | Wyant |
| 5,843,267 A | 12/1998 | Cashaw et al. |
| H1788 H | 2/1999 | Christon et al. |
| 5,865,823 A | 2/1999 | Curro |
| 5,906,603 A | 5/1999 | Roe et al. |

(56) References Cited

U.S. PATENT DOCUMENTS

| | | | |
|---|---|---|---|
| 5,911,713 A | 6/1999 | Yamada et al. | |
| 5,938,648 A | 8/1999 | Lavon et al. | |
| 5,941,864 A | 8/1999 | Roe | |
| 5,947,946 A | 9/1999 | Fisher et al. | |
| 5,968,025 A | 10/1999 | Roe et al. | |
| 6,007,528 A | 12/1999 | Osborn | |
| 6,010,491 A | 1/2000 | Roe et al. | |
| 6,120,487 A | 9/2000 | Ashton | |
| 6,229,061 B1 | 5/2001 | Dragoo et al. | |
| 6,251,097 B1 | 6/2001 | Kline et al. | |
| 6,258,308 B1 | 7/2001 | Brady et al. | |
| 6,278,037 B1 | 8/2001 | Schmidt et al. | |
| 6,287,169 B1 | 9/2001 | Willms et al. | |
| 6,291,039 B1 | 9/2001 | Combe et al. | |
| 6,307,119 B1 | 10/2001 | Cammarota et al. | |
| 6,368,444 B1 | 4/2002 | Jameson et al. | |
| 6,414,215 B1 | 7/2002 | Roe | |
| 6,420,627 B1 | 7/2002 | Ohnishi et al. | |
| 6,423,043 B1 | 7/2002 | Gustafsson | |
| 6,432,098 B1 | 8/2002 | Kline et al. | |
| 6,468,257 B1 | 10/2002 | Ono et al. | |
| 6,482,191 B1 | 11/2002 | Roe et al. | |
| 6,547,773 B2 | 4/2003 | Kleinschmidt et al. | |
| 6,562,016 B2 * | 5/2003 | Shinkai | 604/385.01 |
| 6,575,951 B1 | 6/2003 | Ono et al. | |
| 6,579,273 B2 | 6/2003 | Dupuy | |
| 6,605,071 B1 * | 8/2003 | Gray et al. | 604/385.28 |
| 6,610,901 B2 * | 8/2003 | McMahon-Ayerst et al. | 604/378 |
| 6,623,466 B1 | 9/2003 | Richardson | |
| 6,669,618 B2 | 12/2003 | Reising et al. | |
| 6,680,422 B2 | 1/2004 | Roe | |
| 6,716,441 B1 | 4/2004 | Osborne et al. | |
| 6,764,477 B1 | 7/2004 | Chen et al. | |
| 6,764,478 B2 | 7/2004 | Ashton et al. | |
| 6,786,895 B1 | 9/2004 | Schmitz | |
| 6,794,023 B1 | 9/2004 | Melik et al. | |
| 6,807,685 B1 | 10/2004 | Hasegawa et al. | |
| 6,811,643 B2 | 11/2004 | McAmish et al. | |
| 6,817,992 B1 | 11/2004 | Sassak et al. | |
| 6,821,612 B1 | 11/2004 | Melik et al. | |
| 6,843,949 B2 | 1/2005 | Brady et al. | |
| 6,893,388 B2 | 5/2005 | Reising et al. | |
| 6,980,872 B2 | 12/2005 | Kano et al. | |
| 7,037,569 B2 | 5/2006 | Curro et al. | |
| 7,101,359 B2 | 9/2006 | Kline et al. | |
| 7,166,095 B1 | 1/2007 | Coates | |
| 7,250,549 B2 | 7/2007 | Richlen et al. | |
| 7,264,615 B2 | 9/2007 | Sherrod et al. | |
| 7,344,526 B2 | 3/2008 | Yang et al. | |
| 7,387,620 B2 | 6/2008 | Watanabe et al. | |
| 7,407,468 B2 | 8/2008 | Reising et al. | |
| 7,431,716 B2 * | 10/2008 | Tracy | 604/385.14 |
| 7,458,961 B2 | 12/2008 | Carstens | |
| 7,462,173 B2 | 12/2008 | Carstens | |
| 7,481,801 B2 | 1/2009 | Carstens | |
| 7,491,196 B2 | 2/2009 | Frank et al. | |
| 7,521,587 B2 | 4/2009 | Busam et al. | |
| 7,537,587 B2 | 5/2009 | Carstens | |
| 7,576,019 B2 | 8/2009 | Bond et al. | |
| 7,626,073 B2 | 12/2009 | Catalan | |
| 7,629,501 B2 | 12/2009 | Labit et al. | |
| 7,666,175 B2 | 2/2010 | Trennepohl | |
| 7,695,463 B2 | 4/2010 | LaVon et al. | |
| 7,771,406 B2 | 8/2010 | Mueller et al. | |
| 7,771,408 B2 | 8/2010 | Mueller et al. | |
| 7,776,771 B2 | 8/2010 | Autran et al. | |
| 7,785,309 B2 | 8/2010 | Van Gompel et al. | |
| 7,820,875 B2 | 10/2010 | Roe et al. | |
| 7,833,211 B2 | 11/2010 | Mansfield | |
| 7,914,507 B1 | 3/2011 | Magee | |
| 7,993,322 B2 | 8/2011 | Brud et al. | |
| 8,118,801 B2 | 2/2012 | Macura et al. | |
| 8,158,043 B2 | 4/2012 | Gibson et al. | |
| 2002/0010452 A1 | 1/2002 | Dupuy | |
| 2002/0035747 A1 | 3/2002 | Kusibojoska et al. | |
| 2002/0128619 A1 | 9/2002 | Carlbark et al. | |
| 2003/0091807 A1 | 5/2003 | Desai et al. | |
| 2003/0114805 A1 | 6/2003 | Rainville et al. | |
| 2003/0125701 A1 | 7/2003 | Widlund | |
| 2003/0163104 A1 | 8/2003 | Tears et al. | |
| 2003/0233082 A1 | 12/2003 | Kline et al. | |
| 2004/0023771 A1 | 2/2004 | Reising et al. | |
| 2004/0127867 A1 | 7/2004 | Odorzynski et al. | |
| 2005/0033258 A1 | 2/2005 | Suzuki et al. | |
| 2005/0096624 A1 | 5/2005 | Hoshino et al. | |
| 2005/0131382 A1 | 6/2005 | Brud et al. | |
| 2005/0148974 A1 | 7/2005 | Datta et al. | |
| 2005/0164587 A1 | 7/2005 | Melik et al. | |
| 2005/0177123 A1 | 8/2005 | Catalan | |
| 2005/0215965 A1 | 9/2005 | Schmidt et al. | |
| 2005/0215968 A1 | 9/2005 | Henderson | |
| 2005/0215970 A1 | 9/2005 | Kline et al. | |
| 2005/0215971 A1 | 9/2005 | Roe et al. | |
| 2005/0234411 A1 | 10/2005 | Ashton et al. | |
| 2006/0035055 A1 | 2/2006 | Schneider et al. | |
| 2006/0047260 A1 | 3/2006 | Ashton et al. | |
| 2006/0058766 A1 | 3/2006 | Mueller et al. | |
| 2006/0069372 A1 | 3/2006 | Chakavarty et al. | |
| 2006/0087053 A1 | 4/2006 | O'Donnell et al. | |
| 2006/0107505 A1 | 5/2006 | Desai et al. | |
| 2006/0129114 A1 | 6/2006 | Mason et al. | |
| 2006/0129116 A1 | 6/2006 | Hughes et al. | |
| 2006/0178652 A1 | 8/2006 | Miller | |
| 2006/0189956 A1 | 8/2006 | Catalan | |
| 2006/0229582 A1 | 10/2006 | LaVon | |
| 2006/0247599 A1 | 11/2006 | Mullen et al. | |
| 2006/0264865 A1 | 11/2006 | Carstens | |
| 2006/0264867 A1 | 11/2006 | Carstens | |
| 2006/0264868 A1 | 11/2006 | Carstens | |
| 2006/0264869 A1 | 11/2006 | Carstens | |
| 2006/0264870 A1 | 11/2006 | Carstens | |
| 2006/0264871 A1 | 11/2006 | Carstens | |
| 2006/0264872 A1 | 11/2006 | Carstens | |
| 2006/0264873 A1 | 11/2006 | Carstens | |
| 2006/0264874 A1 | 11/2006 | Carstens | |
| 2006/0264877 A1 | 11/2006 | Carstens | |
| 2006/0264878 A1 | 11/2006 | Carstens | |
| 2006/0264879 A1 | 11/2006 | Carstens | |
| 2006/0264880 A1 | 11/2006 | Carstens | |
| 2006/0264881 A1 | 11/2006 | Carstens | |
| 2006/0264882 A1 | 11/2006 | Carstens | |
| 2006/0264883 A1 | 11/2006 | Carstens | |
| 2006/0264884 A1 | 11/2006 | Carstens | |
| 2006/0264885 A1 | 11/2006 | Carstens | |
| 2006/0282056 A1 | 12/2006 | McDonald | |
| 2006/0293637 A1 | 12/2006 | La Von et al. | |
| 2007/0005038 A1 | 1/2007 | Mansfield et al. | |
| 2007/0032772 A1 | 2/2007 | Ehrnsperger et al. | |
| 2007/0142798 A1 | 6/2007 | Goodlander et al. | |
| 2007/0142816 A1 | 6/2007 | Carstens | |
| 2007/0191806 A1 | 8/2007 | Mueller et al. | |
| 2007/0239130 A1 | 10/2007 | Trennepohl | |
| 2008/0033388 A1 | 2/2008 | Mueller et al. | |
| 2008/0114320 A1 | 5/2008 | Beck et al. | |
| 2008/0114327 A1 * | 5/2008 | Barge | 604/396 |
| 2008/0119813 A1 | 5/2008 | Carstens | |
| 2008/0119816 A1 | 5/2008 | Carstens | |
| 2008/0125737 A1 * | 5/2008 | Modgeddi et al. | 604/385.01 |
| 2008/0224351 A1 | 9/2008 | Curro et al. | |
| 2008/0287983 A1 | 11/2008 | Smith et al. | |
| 2008/0312617 A1 | 12/2008 | Hundorf et al. | |
| 2008/0312618 A1 | 12/2008 | Hundorf et al. | |
| 2008/0312619 A1 | 12/2008 | Ashton et al. | |
| 2008/0312620 A1 | 12/2008 | Ashton et al. | |
| 2008/0312621 A1 | 12/2008 | Hundorf et al. | |
| 2008/0312622 A1 | 12/2008 | Hundorf et al. | |
| 2008/0312623 A1 | 12/2008 | Hundorf et al. | |
| 2008/0312624 A1 | 12/2008 | Hundorf et al. | |
| 2008/0312625 A1 | 12/2008 | Hundorf et al. | |
| 2008/0312628 A1 | 12/2008 | Hundorf et al. | |
| 2009/0048571 A1 | 2/2009 | Spitzmueller et al. | |
| 2009/0127742 A1 | 5/2009 | Qureshi et al. | |
| 2009/0133446 A1 * | 5/2009 | Burrow et al. | 66/176 |

(56) References Cited

U.S. PATENT DOCUMENTS

| | | | |
|---|---|---|---|
| 2009/0317584 A1* | 12/2009 | Ivanoff et al. | 428/95 |
| 2010/0005570 A1 | 1/2010 | Rachman | |
| 2010/0179495 A1 | 7/2010 | Roe et al. | |
| 2010/0179496 A1 | 7/2010 | Roe et al. | |
| 2010/0179498 A1 | 7/2010 | Roe | |
| 2010/0179499 A1 | 7/2010 | Roe | |
| 2010/0179500 A1 | 7/2010 | Roe et al. | |
| 2010/0179501 A1 | 7/2010 | Roe et al. | |
| 2010/0179502 A1 | 7/2010 | Roe | |
| 2010/0179503 A1 | 7/2010 | Roe | |
| 2010/0201024 A1 | 8/2010 | Gibson et al. | |
| 2010/0249736 A1* | 9/2010 | Png et al. | 604/365 |
| 2011/0172628 A1 | 7/2011 | Roe et al. | |
| 2012/0022481 A1 | 1/2012 | Roe et al. | |
| 2012/0049404 A1 | 3/2012 | Gibson et al. | |

FOREIGN PATENT DOCUMENTS

| | | |
|---|---|---|
| CA | 2 221 209 | 11/1996 |
| CA | 2 365 577 | 6/2003 |
| CN | 1505531 A | 6/2004 |
| CN | 1285727 A | 11/2006 |
| DE | 103 03 903 | 11/2003 |
| EP | 0 023 804 | 2/1981 |
| EP | 0 187 726 | 7/1986 |
| EP | 0 319 314 | 6/1989 |
| EP | 0 811 362 A1 | 12/1997 |
| EP | 0 549 988 | 6/1998 |
| EP | 0 796 069 | 8/2000 |
| EP | 0 763 353 | 6/2002 |
| EP | 2 106 775 | 10/2009 |
| FR | 2532337 A1 | 3/1984 |
| FR | 2606257 A1 | 5/1988 |
| GB | 0 112 638 A | 1/1918 |
| GB | 2 440 314 | 1/2008 |
| JP | 55-37849 U | 9/1978 |
| JP | 57-138908 | 8/1982 |
| JP | 57-181003 | 11/1982 |
| JP | 57-184864 | 12/1982 |
| JP | 59-5656 | 1/1984 |
| JP | 59-5657 | 1/1984 |
| JP | 59-147214 | 9/1984 |
| JP | 59-147215 | 9/1984 |
| JP | 60-87139 | 6/1985 |
| JP | 60-91191 | 6/1985 |
| JP | 61-98628 | 6/1986 |
| JP | 61-168103 U | 10/1986 |
| JP | 62-110903 | 7/1987 |
| JP | 63-196701 A | 8/1988 |
| JP | 03-091325 | 1/1990 |
| JP | 04-77922 | 11/1990 |
| JP | 06-178795 | 1/1993 |
| JP | 06-63077 A | 3/1994 |
| JP | 30-73695 | 9/2000 |
| JP | 2001-353183 A1 | 12/2001 |
| JP | 2002-95698 A | 4/2002 |
| JP | 2002-325786 | 11/2002 |
| JP | 2003-038564 | 2/2003 |
| JP | 2003-190213 A | 7/2003 |
| JP | 2005-6827 | 1/2005 |
| JP | 2005-111119 | 4/2005 |
| JP | 31-09189 | 5/2005 |
| JP | 2007-244506 | 3/2006 |
| JP | 2007-68654 A | 3/2007 |
| JP | 2008-055002 A | 3/2008 |
| WO | WO 90/08524 | 8/1990 |
| WO | WO 91/16871 | 11/1991 |
| WO | WO 92/01431 | 2/1992 |
| WO | WO 92/15444 | 9/1992 |
| WO | WO 94/15563 | 7/1994 |
| WO | WO 94/15663 | 7/1994 |
| WO | WO 95/10992 | 4/1995 |
| WO | WO 95/16746 | 6/1995 |
| WO | WO 96/17572 | 6/1996 |
| WO | WO 96/24319 | 8/1996 |
| WO | WO 96/32912 | 10/1996 |
| WO | WO 97/24095 | 7/1997 |
| WO | WO 00/65348 | 11/2000 |
| WO | WO 01/34080 A2 | 5/2001 |
| WO | WO 02/066086 | 8/2002 |
| WO | WO 2004/060229 | 7/2004 |
| WO | WO 2005/039469 | 5/2005 |
| WO | WO 2005/052052 | 6/2005 |
| WO | WO 2005/096855 | 10/2005 |
| WO | WO 2005/097031 | 10/2005 |
| WO | WO 2008/030984 | 3/2008 |
| WO | WO 2008/120959 | 10/2008 |
| WO | WO 2008/142634 | 11/2008 |
| WO | WO 2010/053006 | 5/2010 |
| WO | WO 2010/111717 | 9/2010 |
| WO | WO 2010/113071 | 10/2010 |
| WO | WO 2010/134169 | 11/2010 |
| WO | WO 2010/135510 | 11/2010 |
| WO | WO 2011/047252 | 4/2011 |
| WO | WO 2011/047264 | 4/2011 |

OTHER PUBLICATIONS

PCT International Search Report and Written Opinion dated Mar. 27, 2011, 26 pages.
www.gdiapers.com—Web pages dated Nov. 23, 2009.
www.fuzzibunz.com—Web pages dated Nov. 23, 2009.
www.greenmountaindiapers.com—Web pages dated Nov. 23, 2009.
www.bumgenius.com—Web pages dated Nov. 23, 2009.
www.thirstiesbaby.com—Web pages dated Nov. 23, 2009.
www.crickettsdiaper.com—Web pages dated Nov. 23, 2009.
Archived web page from www.bummis.com, Aug. 8, 2005, obtained via www.waybackmachine.org.
"Green Life; Earth-Friendly Disposable Diaper Lets Parents Flush Away the Guilt", The Oregonian (Apr. 7 2005).
"Crazy for Cloth: The Benefits of Cotton Diapers", Mothering Magazine (Jan. 1, 2003).
"Not Your Grandma's Diapers", E: The Environmental Magazine (Mar.-Apr. 2006).
"Y2K Babyware: Your Green Guide to Carefree Diapering for Your Millennium Bundle of Joy". The Gazette (Montreal, Quebec) (Oct. 5, 2000).
"The Evolution of Diapers: Cloth Meets Cute for Some Mothers (and Grandmothers), The Changes in Cloth Diapers Have Made Them all the Rage. Learning the Lingo Navigating Cloth" Omaha World Herald (Mar. 22, 2004).
37 photographs (obtained from Marketing Technology Service, Inc.) of a product believed to be a product of Kao Corp. and sold in Japan in 1986 (translations provided by Applicants.
Data Sheet, p. V-17, from "Baby Diaper Design Update—1987"; publication of Marketing Technology Service, Inc., product believed to be a product of Kao Corp. sold. in Japan in 1986 or 1987.

* cited by examiner

OUTER COVER FOR AN ABSORBENT ARTICLE

CROSS REFERENCE TO RELATED APPLICATIONS

This application claims the benefit of U.S. Provisional Application No. 61/366,670, filed Jul. 22, 2010, and U.S. Provisional Application No. 61/484,782, filed May 11, 2011, both of which are hereby incorporated by reference in their entireties.

FIELD OF THE INVENTION

This disclosure relates generally to an outer cover for an absorbent article, and more specifically to an outer cover with liquid absorptive capacity.

BACKGROUND OF THE INVENTION

Absorbent articles fitted to the body of a wearer are sometimes used to absorb body exudates, such as urine, feces, or menses. Absorbent articles may be used, for example, by infants who have not been toilet trained, or by children or adults experiencing incontinence due to illness or infirmity, or by menstruating women. Absorbent articles may be disposable or reusable, or a combination of the two. For example, an absorbent article may have a disposable absorbent insert for collecting and containing body fluids, and a reusable outer cover which holds the disposable absorbent insert near the body of the wearer during use.

A disposable absorbent insert may be intended to capture all body exudates; however, some volume of exudates may not be absorbed by the insert, or may not be absorbed immediately. For example, the absorbent capacity of the insert may be exceeded in at least a portion of the insert; or a release of exudates may occur at a rate greater than the maximum rate of absorption of the insert; or the position of the insert relative to the body of the wearer may be such that a small amount of fluid is not directed to the insert, but rather moves beyond the insert and into the outer cover. In such situations, it may be desirable that the outer cover keeps these exudates contained within the absorbent article. Containment may, for example, prevent the soiling of nearby surfaces in the wearer's environment, such as the wearer's clothes, a caregiver's clothes, bedding, furniture, and the like.

One approach to containing such loose substances within the absorbent article is to use a hydrophobic outer cover and secure it tightly to the wearer, particularly around the legs and waist, as by elastic leg bands and waist bands. However, liquid or semi-liquid wastes may pool and collect along the edges of a hydrophobic material, such that any gapping at the leg or waist bands will allow errant wastes to escape. Further, tight closures may be uncomfortable, constrain wearer movement, leave red marks on or abrade the skin, limit the adaptability of a single size of an outer cover to fit a range of wearer shapes and sizes, or have other limitations.

There remains a need for an outer cover for an absorbent article which is comfortable, conformable to a wearer, and contains exudates not absorbed by the absorbent insert within the absorbent article.

SUMMARY OF THE INVENTION

In some aspects, the invention relates to an outer cover for an absorbent article. The outer cover may comprise a first, wearer-facing layer having a wearer-facing surface, and a second, garment-facing layer. The outer cover may have an absorbent capacity between 5 and 100 g, and the wearer-facing surface of the first, wearer-facing layer may have a DAT contact angle at 0.5 second of less than about 75 degrees. The second, garment-facing layer may be hydrophobic. The outer cover as a whole may have a WVTR between 1,200 $g/m^2/24$ hr and 15,000 $g/m^2/24$ hr, or between 3,000 $g/m^2/24$ hr and 10,000 $g/m^2/24$ hr. The wearer-facing surface of the first, wearer-facing layer may have a nonpolar component of surface energy of less than about 3.5 $mJ/mm^2$, or less than about 3.0 $mJ/mm^2$, or less than about 2.5 $mJ/mm^2$. The wearer-facing surface of the first, wearer-facing layer may have a DAT contact angle at 1 second of less than about 70 degrees, or less than about 45 degrees. The first, wearer-facing layer may have a strikethrough time of less than about 15 seconds, or less than about 10 seconds, or between 1 and 15 seconds. The outer cover may comprise a third layer disposed between the first, wearer-facing layer and the second, garment-facing layer. The third layer, if present, may be hydrophobic.

In other aspects, the invention relates to an outer cover for an absorbent article, the outer cover consisting of a single layer or laminate of material. The outer cover may comprise a first, wearer-facing surface and a second, garment-facing surface. The outer cover may have an absorbent capacity between 5 and 100 g. The first, wearer-facing surface may have a DAT contact angle at 0.5 second of less than about 75 degrees. The second, garment-facing surface may be hydrophobic. The outer cover may have a WVTR between 1,200 $g/m^2/24$ hr and 15,000 $g/m^2/24$ hr, or between 3,000 $g/m^2/24$ hr and 10,000 $g/m^2/24$ hr. The outer surface may be coated with a water resistant compound. The water resistant compound, if present, may be selected from the group consisting of polytetrafluoroethylene, fluorocarbon derivatives, hydrophobic silicone polymers, hydrophobic fluorinated polymers, and combinations thereof.

In still other aspects, the invention relates to an absorbent article comprising an absorbent insert and an outer cover, wherein the outer cover may have an absorbent capacity greater than 0 and less than an absorbent capacity of the absorbent insert.

DETAILED DESCRIPTION OF THE INVENTION

Figure 1:
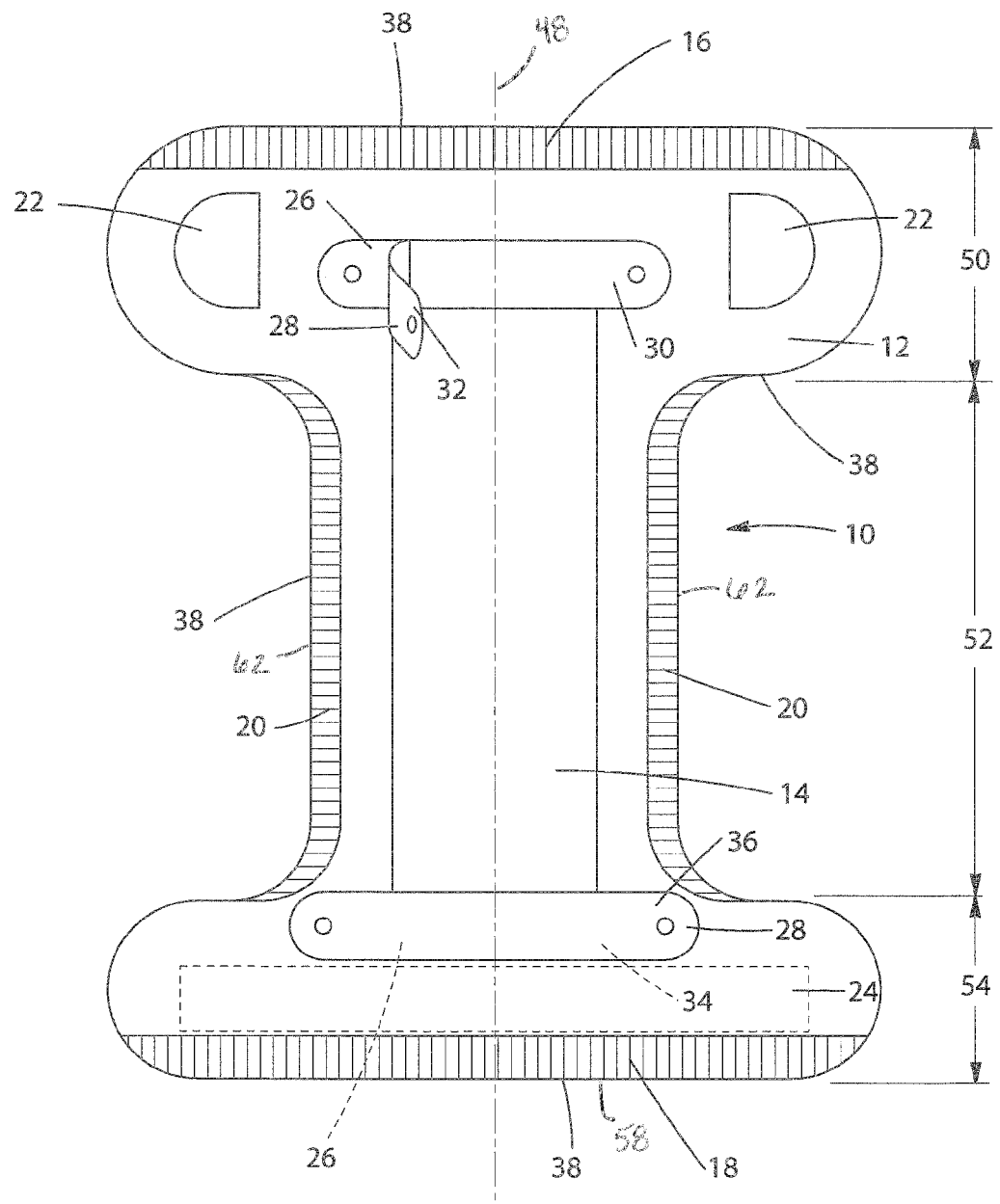
FIG. 1 is a plan view of an exemplary absorbent article.

As used herein, "absorbent article" refers to devices which absorb and contain body exudates and, more specifically, refers to devices which are placed against or in proximity to the body of a wearer to absorb and contain various exudates discharged from the body. Exemplary absorbent articles include diapers, training pants, pull-on or pant-type diapers (i.e., a diaper having a pre-formed waist opening and leg openings such as illustrated in U.S. Pat. No. 6,120,487), refastenable diapers, incontinence briefs and undergarments, diaper holders and liners, feminine hygiene garments such as sanitary napkins and panty liners, and the like. An absorbent article may be disposable or reusable.

As used herein, "absorbent insert" refers to a component of an absorbent article used to capture or contain body exudates, and which is removably associated with the absorbent article during use. For example, an absorbent insert may be press-fit into place, or may be releasably attached to some portion of the absorbent article, as by mechanical fasteners, adhesives, cohesives, and the like. An absorbent insert may be disposable or reusable.

As used herein, "disposable" refers to an article or object which is intended to be used once, or for one continuous time period of usage, and then discarded. A disposable article is not intended to be cleaned, repaired, or otherwise prepared for reuse. In contrast, a reusable article is intended to be used at least twice, and may be intended for repeated use over an extended period of time, such as weeks or months. A reusable article may be cleaned, repaired, or otherwise restored prior to reuse.

For example, a reusable article may be used, laundered, and reused. A single article may include disposable components and reusable components. For example, an absorbent article may comprise a reusable outer cover and a disposable absorbent insert.

As used herein, "wearer-facing" or "inner" refers to the side or surface of an absorbent article or a component of an absorbent article which is nearest the body of a wearer, when the absorbent article is applied to the wearer as intended for normal use. In contrast, "garment-facing" or "outer" refers to the side or surface of an absorbent article or a component of an absorbent article opposite the wearer-facing side, and nearest the wearer's clothes, if the wearer is wearing clothes over the absorbent article, when the absorbent article is applied to the wearer as intended for normal use.

As used herein, "hydrophilic" describes surfaces which are wettable by aqueous fluids (e.g., aqueous body fluids) deposited on these surfaces. Hydrophilicity and wettability are typically defined in terms of contact angle on a nonwoven fabric. A surface is said to be wetted by a fluid (i.e., hydrophilic) when the contact angle between the fluid and the surface is less than 90°, as measured at 0.2 seconds using the Dynamic Absorption Test described below. Conversely, a surface is considered to be "hydrophobic" if the contact angle is greater than 90° as measured at 0.2 seconds using the Dynamic Absorption Test described below.

As used herein, "insult" refers to exposure of an article to a body exudate, and may also be referred to as an event or an exposure. An absorbent insert may be changed or discarded after a single insult, for example, after a single act of defecation. An absorbent insert may be changed or discarded after several insults, such as several discrete acts of urination and/or defecation.

As used herein, "outer cover" refers to a component of an absorbent article used to hold the absorbent article against or near a wearer's body. An outer cover may also hold an absorbent insert in place relative to the wearer, or the absorbent article, or both. An outer cover may have one or more layers or components. If the outer cover comprises multiple layers or components, the term "outer cover" refers collectively to all the layers or components which would be assembled to hold an absorbent insert and absorbent article against or near a wearer's body during normal use, i.e., during use according to the manufacturer's instructions.

As shown in FIG. 1, an absorbent article 10 may be formed, in whole or in part, by an outer cover 12 and an absorbent insert 14. Outer cover 12 may serve to hold absorbent article 10 against the body of a wearer, for example, by wrapping around the wearer's legs and torso. Absorbent insert 14 may serve to absorb and contain body exudates, such as urine, feces, or menses, discharged by the wearer into absorbent article 10. Outer cover 12 and absorbent insert 14 may each, independently, be reusable or disposable. For example, absorbent article 10 may have a reusable outer cover 12 and a disposable absorbent insert 14. When disposable absorbent insert 14 is soiled, it may be discarded, and a new disposable absorbent insert 14 may be fitted to reusable outer cover 12. It is also possible to have a disposable outer cover 12 and reusable absorbent insert 14, or absorbent articles 10 wherein the outer cover 12 and absorbent insert 14 are both reusable, or both disposable.

Outer cover 12 may comprise elastic elements, such as elasticized rear waistband 16, elasticized front waistband 18, or elasticized leg bands 20, to help conform absorbent article 10 to a wearer. Outer cover 12 may comprise fasteners 22, which may be permanently or releasably joined to a landing zone 24, to form a waist opening. Fasteners 22 may comprise almost any fastening system, including, but not limited to, adhesives, cohesives, snaps, ties, zippers, buttons, hook-and-loop, hook-and-hook, tab-and-slot, magnets, sewn stitches, or combinations of these fasteners. Landing zone 24, if present, may be adapted to receive fasteners 22. For example, fasteners 22 may comprise hooks and landing zone 24 may comprise loops, or fasteners 22 may comprise and adherent and landing zone 24 may comprise an adherend, or fasteners 22 may comprise button holes and landing zone 24 may comprise one or more buttons. Landing zone 24 may be disposed on the garment-facing surface of absorbent article 10, as shown in FIG. 1. However, in some embodiments, landing zone 24 may be disposed on the wearer-facing surface of absorbent article 10, or on a layer disposed between the garment-facing surface and the wearer-facing surface of absorbent article 10. For example, fasteners 22 may be folded inside absorbent article 10 to contact landing zone 24, or the fastening system may include elements such as magnets, which do not require direct contact between fasteners 22 and landing zone 24 to function.

Outer cover 12 may further comprise one or more connectors 26. Connectors 26 may be adapted to permanently or releasably join absorbent insert 14 to outer cover 12. Connectors 26 may include almost any fastening system, as described above. For examples, connectors 26 may comprise adhesives which adhere the garment-facing surface of absorbent insert 14 to the wearer-facing surface of outer cover 12. Absorbent insert 14 may comprise connectors 28 to facilitate joining absorbent insert 14 to outer cover 12. For example, connectors 28 may comprise hooks and connectors 26 may comprise loops, or connectors 26 and 28 may comprise complementary cohesives. In some embodiments, absorbent insert 14 comprises one or more connectors 28, and outer cover 12 has no connectors. Connectors 28 and 26 may have the same or different shapes and dimensions. In some embodiments, outer cover 12 may have no distinct connectors 26. For example, outer cover 12, or inner surface 40 of outer cover 12, may have a relatively high static coefficient of friction relative to absorbent insert 14, such that absorbent insert 14 does not tend to move against outer cover 12. The static coefficient of friction may be varied by adding coatings or layers having a high coefficient of friction, by mechanically deforming the substrate to create a rougher surface, or by any other means. Static coefficient of friction may be measured as described below, and may vary from 0.3 to 0.4 or 0.5 or higher over inner surface 40 of outer cover 12.

Figure 2:
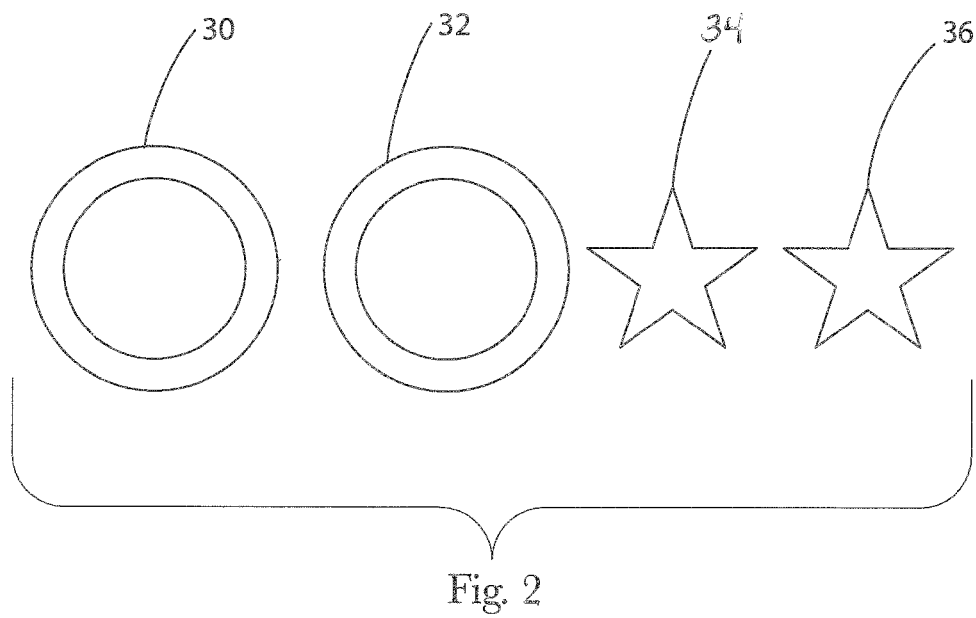
FIG. 2 is a schematic view of exemplary fasteners.

In some embodiments, outer cover 12 comprises two or more connectors 26. A first connector 30 may have a different shape or dimension than at least a second connector 34. In some embodiments, absorbent insert 14 comprises two or more connectors 28. A first connector 32 may have a different shape or dimension than at least a second connector 36. First connector 30 in outer cover 12 may have a shape and size complementary to, or similar to, or the same as, first connector 32 in absorbent insert 14. Second connector 34 in outer cover 12 may have a shape and size complementary to, or similar to, or the same as, second connector 36 in absorbent insert 14. In such an embodiment, the proper orientation of absorbent insert 14 relative to outer cover 12 may be indicated by the different shapes or dimensions of the first and second connectors. For example, if absorbent insert 14 has a front side and a back side, the shape or size of the connectors may indicate that the front of absorbent insert 14 should be placed near the front of outer cover 12. In some embodiments, the position, dimensions, or shapes of the first and second connectors interact such that absorbent insert 14 can only be joined to outer cover 12 in a desired orientation, as shown in FIG. 2, where second connectors 34 and 36 would not substantially interact with first connectors 30 and 32 in a manner that would securely join absorbent insert 14 to outer cover 12. In some embodiments, the first and second connectors are of different types, so that it is not possible to secure absorbent insert 14 to outer cover 12 except in the desired orientation. For example, the first connectors may form a hook-and-loop system, and the second connectors may form a cohesive system.

Absorbent insert 14 may be intended to capture and contain all wastes eliminated by the wearer in the covered region of the body. However, some relatively small quantities of bodily exudates, such as urine, may occasionally evade absorbent insert 14 and contact the wearer-facing surface of outer cover 12. If the wearer-facing surface of outer cover 12 cannot absorb the fluid, the fluid may move along the wearer-facing surface of outer cover 12 and breach the perimeter 38 of absorbent article 10, thereby leaking onto clothing or other surfaces, such as bedding, carpeting, or a caregiver. In some embodiments, outer cover 12 has an absorbent capacity less than the absorbent capacity of absorbent insert 14. In some embodiments, outer cover 12 may have a fluid absorbent capacity between 5 and 100 mL, or between 20 and 60 mL, as measured by the Centrifuge Retention Capacity (CRC) test, described below, when testing the entire outer cover. CRC results may also be reported in a "unitized" or normalized format, wherein the result is reported as the total measured retention capacity of a sample divided by the weight of the dry sample prior to testing. Outer cover 12 may have a unitized CRC greater than 0.5 g/g, or between 0.5 g/g and 1.0 g/g.

Figure 3:
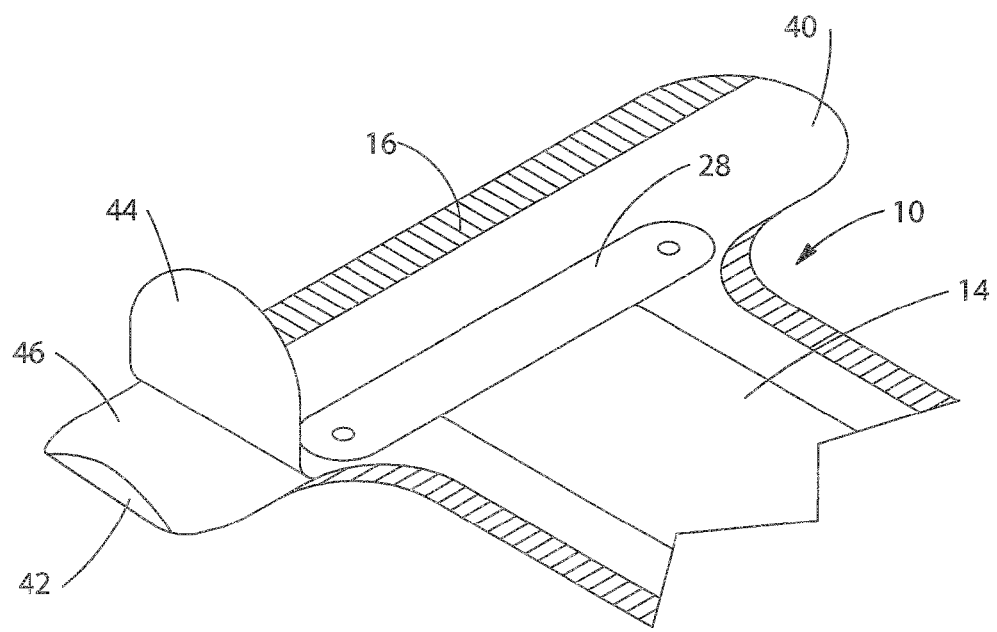
FIG. 3 is a perspective view of a portion of an exemplary absorbent article.

Outer cover 12 may be constructed of a unitary element, such as a single layer of material, or a bonded laminate of two or more materials. In some embodiments, as shown in FIG. 3, outer cover 12 may be constructed of two or more discrete layers of material, such as inner, wearer-facing layer 44 and outer, garment-facing layer 46, having similar or different properties. If outer cover 12 is constructed of two or more discrete layers, the two or more discrete layers of material may be joined together at or near the perimeter 38 of absorbent article 10, e.g., in a seam or attachment point of a leg or waistband, or may be joined at one or more discrete locations in the article, such as at locations where a connector 26 or fastener 22 is affixed to inner surface 40 or outer surface 42 of outer cover 12. If outer cover 12 comprises two or more layers, it should be understood that each layer has a wearer-facing surface and a garment-facing surface.

In some embodiments, inner surface 40 of outer cover 12 is absorbent, and any absorbed fluid does not wet through to outer surface 42 of outer cover 12, i.e., the garment-facing surface, under normal wearing conditions. Nonetheless, outer cover 12 may be breathable to prevent over-hydration of the wearer's skin. Over-hydration of the skin may be caused, or exacerbated, by high localized humidity between absorbent article 10 and a wearer's skin. Over-hydrated skin may exhibit erythema (redness), or diaper dermatitis, or may be less resistant to abrasion (i.e., from a lower tensile strength) than skin which is not over-hydrated. Outer cover 12 may have a minimum breathability, or Water Vapor Transmission Rate (WVTR) as measured by the Water Vapor Transmission Rate test described below, to allow sufficient water vapor from urine, sweat and/or other exudates to leave the interior of absorbent article 10, maintaining the skin hydration at a lower level. Outer cover 12 may have a WVTR of at least about 1200 g/m$^2$/24 hr, or a WVTR of at least about 3000 g/m$^2$/24 hr. Higher WVTRs may be helpful, for example, when the ambient conditions are higher in temperature and/or humidity, when the wearer is more active (e.g., perspires more), or when absorbent article 10 has a relatively high load of urine, sweat, or other liquid exudates (e.g., during overnight use, or when the user is a "heavy wetter"). Thus, a WVTR of at least about 1200 g/m$^2$/24 hr may indicate a serviceable outer cover in typical use, while a WVTR of at least about 3000 g/m$^2$/24 hr may indicate a serviceable outer cover under more challenging conditions.

In certain instances, too high a breathability can have undesirable effects, such as moisture condensation, on the garment-facing surface of the article or on clothing. Outer cover 12 may have a WVTR of less than about 15,000 g/m$^2$/24 hr, or even 10,000 g/m$^2$/24 hr, to help prevent this phenomenon. A lower maximum WVTR indicates a serviceable outer cover under challenging conditions, such as lower ambient temperatures, where escaping water vapor may generate more condensation than at relatively higher ambient temperatures.

The outer surface 42 of a single layer outer cover material may be hydrophobic. The hydrophobicity of outer surface 42 may result, for example, from the choice of fiber/yarn chemistry or diameter in the substrate, the manner in which the yarns are woven or knitted, or in coatings or other treatments applied to the yarns, finished material, or both. For example, outer surface 42 may be blended (as with micro or nanofibers), coated, or otherwise treated with water resistant compounds, such as polytetrafluoroethylene (also known as PTFE, or TEFLON); fluorocarbon derivatives (also known as SCOTCHGARD, as described, for example, in U.S. Pat. No. 3,574,791); or a hydrophobic silicone polymer or fluorinated polymer (such as those described, for example, in U.S. Pat. No. 7,626,073), or the like. In outer cover embodiments comprising two or more layers of material, garment-facing layer 46 (i.e., the outermost layer), or either surface thereof, may be hydrophobic or treated to become hydrophobic via any of the treatments or methods described herein. Alternatively, the garment-facing surface of inner layer 44 may be treated to be hydrophobic, or a third, hydrophobic layer may be disposed between inner layer 44 and outer layer 46 of outer cover 12.

The inner layer 44 or inner surface 40 of outer cover 12 may be treated to make it hydrophilic, or to increase its hydrophilicity. For example, inner layer 44 or inner surface 40 may be treated with surfactants or other coatings that confer or improve hydrophilicity. For example, inner layer 44 or inner surface 40 may be treated with a solution comprising nanoparticles, as described in US Patent Application Publication 2009/0048571. The solution may comprise a film-forming polymer, a wetting agent, and from about 0.001% to about 40% by weight of the composition of nanoparticles. The nanoparticles may be selected from the group consisting of alumina, silica, and combinations thereof. The nanoparticles may have a particle size from about 1 to about 750 nanometers. The weight ratio of the film forming polymer to the nanoparticles may be from about 1:1 to about 1:30. Exemplary film-forming polymers include, but are not limited to, polyamines, quaternized polyamines, zwitterionic polymers; polycarboxylates; polyethers; polyhydroxylated polymers; polyphosphonates and polyphosphates; polymeric chelants; ethoxylated or alkoxylated polyamines; polycarboxylated polyamines; water dispersible polyethers; water dispersible polyhydroxylated groups or polymers, including polysaccharides; water dispersible polycarboxylates; water dispersible anionic groups such as carboxylates, sulfonates, sulfates, phosphates, phosphonates and polymers thereof; dispersible polystyrenes containing anionic groups such as carboxylates, sulfonates, sulfates, phosphates, phosphonates and polymers thereof; water dispersible polymers containing groups of amines, quaternaries, amine oxides and combinations thereof; water dispersible zwitterionic groups and polymers thereof; water dispersible amides and polyamides; and water dispersible polymers and copolymers of vinylimidazole and vinylpyrrolidone; polymer and block co-polymer combinations of the above.

As another example, inner layer 44 or inner surface 40 may be treated with hydrophilic monomers and radical polymerization initiators, as described in U.S. Pat. No. 7,521,587. The monomers may contain at least one unsaturated double bond according to the general formula $R1R2C=CR3R4$, with R1 and R2 preferably being hydrogen atoms. In some embodiments, the hydrophilic monomers comprise a group which can react with an acid or base to form a salt. Examples of suitable monomers include acrylic acid and its derivates (e.g., methacrylic acid, ethylacrylic acid), styrene sulphonic acid and its derivates, vinyl acetate, maleic anhydride and vinyl pyridine. The initiator may be capable of forming reactive radicals upon activation with light. Examples of suitable radical polymerization initiators include benzophenone and its derivates, benzoyl peroxide, or azobisisobutyronitrile (AIBN). The coating solution may further comprise an agent which reduces homopolymerization of the hydrophilic monomers, such as iron-II salts, copper-II-salts, or mixtures thereof. The coating solution may be applied to the fibers, and the coated fibers may be exposed to UV light, such as UV-A light, to form hydrophilic polymers which are chemically grafted to the fibers.

In some embodiments, inner layer 44 or inner surface 40 of outer cover 12 may be treated to increase hydrophilicity, and outer layer 46 or outer surface 42 of outer cover 12 may be treated to increase hydrophobicity. In addition to the exemplary hydrophilic and hydrophobic treatments described herein, virtually any hydrophilic or hydrophobic treatment could be used. Durable treatments may be selected, for example, if outer cover 12 is intended to be reusable, or to reduce the possibility of transferring the coating or treatment to the wearer of outer cover 12.

Inner surface 40 of outer cover 12 may have a Contact Angle at 0.5 second, as measured by the Dynamic Absorption Test disclosed herein, of less than about 90 degrees, or less than about 75 degrees. The Contact Angle at 0.5 second may be in the range of about 45 and about 90 degrees. The outer cover may have a Contact Angle at 1.0 second of less than about 80 degrees, or less than about 45 degrees. In addition to the treatments discussed above, increasing the three-dimensionality of a surface, as discussed below, may lead to a reduction in the contact angle of the material. Increasing the porosity or capillarity of a surface, as may be done, for example, to increase breathability, may also lead to a reduction in the contact angle of the material.

Inner surface 40 of outer cover 12 may have a Strikethrough time, as measured by the method disclosed herein, of less than about 15 seconds, less than about 10 seconds, or between about 1 second and 15 seconds. Low strikethrough times represent faster penetration of fluid into outer cover 12, which reduces free fluid available to escape outer cover 12 and soil the environment.

Inner surface 40 of outer cover 12 may have a nonpolar component of surface energy, as measured by the Surface Free Energy test disclosed herein, of less than about 3.5, less than about 3.0, or less than about 2.5 $mJ/mm^2$. A lower nonpolar component of surface energy may be associated with a lower tendency to stain when contacted by fatty substances. Although urine is typically predominantly aqueous, feces and other exudates may contain fats or fatty substances. Non-aqueous or lipophilic stains are generally difficult to remove from surfaces such as textiles during common water-based washing processes typically employed in domestic laundry facilities, such as laundry facilities in private homes or launderettes. Surfaces which are at least initially more resistant to lipophilic staining may have a relatively low nonpolar surface energy component, for example, a nonpolar surface energy component less than 10 $mJ/mm^2$, or less than 5 $mJ/mm^2$, or less than 3 $mJ/mm^2$ Outer cover 12 may be soft, so as to not abrade the wearer's skin. Perception of softness may involve a complex set of variables. However, for both flexible and resilient surfaces, a surface having a three-dimensional configuration on a microscale may be perceived as softer than a more two-dimensional configuration of the same material composition. A three-dimensional configuration may be created, or selected for, with various weaves of woven fabrics. For example, woven fabrics may be created or selected having relatively high warp and weft heights, yarn spacing, etc. Tighter weaves (i.e., lower spacing between yarns) may have a more dominant effect on surface energy.

Outer cover 12 may fit the contours of the wearer's body. Outer cover materials may have a low bending stiffness to enable them to adapt and conform to the wearer's anatomy and move with the wearer's body with relatively low resistance, which may contribute to a comfortable fit whether the wearer is quiescent or active. A conforming fit may also allow the perimeter region of the outer cover, which may include elasticized leg or waist bands, to remain in a desirable orientation and location on the wearer's body. Maintaining a desirable orientation and location may help prevent or reduce leakage of bodily exudates from outer cover 12.

As discussed above, outer cover 12 may be constructed of a unitary element, such as a single layer of material or a bonded laminate of two or more materials. Alternatively, outer cover 12 may be constructed of two or more discrete layers of material, having similar or different properties. If outer cover 12 is constructed of two or more discrete layers of material, the two or more discrete layers of material may be joined together at or near the perimeter of the article, e.g., in a seam or attachment point of a leg or waistband, or may be joined at one or more discrete locations in the article, such as at locations where a fastening element, such as fastener 22 or connector 26, is affixed to the inner surface 40 or outer surface 42 of outer cover 12. Regardless of the number of layers, or "stack up", the bending stiffness of the stack up of outer cover 12 material may be less than about 0.20 N, or 0.19 N, in the Bending Stiffness test described herein. If outer cover 12 includes more than one discrete layer (i.e., separable from another layer of the outer cover over a sufficient area to enable the Bending Stiffness test to be performed, the Bending Stiffness of at least one of the layers may be less than about 0.10 N or less than about 0.08 N. In some embodiments, each layer may have a Bending Stiffness of less than about 0.10 N or 0.08 N.

The addition of a fastening element to the wearer-facing surface of the outer cover may require, in some embodiments, a higher Bending Stiffness to create additional support to carry the loading force transferred from insert 14 to the outer cover material. The Bending Stiffness of the "as used" stack up of outer cover material to which an insert-to-outer cover material is affixed may be less than about 0.30 N.

In some embodiments, outer cover 12 may comprise a different layer structure in different regions. For example, outer cover 12 may have a longitudinal centerline 48. Outer cover 12 may have three portions of approximately equal lengths along longitudinal centerline 48. Rear portion 50, for example, may occupy approximately one-third of the length of outer cover 12 from the laterally extending rear longitudinal edge 56, front portion 54 may occupy approximately one-third of the length of outer cover 12 from the laterally extending front longitudinal edge 58, and central portion 52 may occupy approximately one-third of the length of outer cover 12 between rear portion 50 and front portion 54.

The rear portion 50, center portion 52, and front portion 54 of outer cover 12 may desirably have different properties. For example, regions of outer cover 12 corresponding to the wearer's waist, hips, and buttocks regions, generally in rear portion 50 and front portion 54, may be subjected to tensile and bending/torsional stresses during application and/or wearing of absorbent article 10. In contrast, center portion 52 may be subject to stresses different in direction and magnitude related to the mass of exudates contained by the diaper as it is soiled. Center portion 52 may also be more likely to be soiled by exudates during use, including wearing absorbent article 10 and changing absorbent insert 14. Accordingly, it may be desirable, for example, for center portion 52 to extend less than rear portion 50 and/or front portion 54 under similar tensile forces. This could allow rear portion 50 and/or front portion 54 to comfortably fit the waist and hips of a range of users, or of a single user over a period in which the user grows or gains weight, while providing additional support for absorbent insert 14 in center portion 52, such that a heavily soiled absorbent insert 14 does not cause outer cover 12 to sag to a degree that gaps are created along the legs. Gaps along the legs could make it more likely that exudates would leak from absorbent article 12.

In some embodiments, different portions of the outer cover may have different properties due to different layers of materials. The layers may be different in the number of layer(s), the kinds of layers (e.g., material, basis weight, texture, treatment, etc.), or both. For example, rear portion 50 and center portion 52 may comprise the same material, such as the material used in Example 1, but there may be only one layer of the material in rear portion 50 and two, or more, layers of the material in center portion 52. This would provide lower extension under tension in center portion 52 and increased resistance to penetration of wearer exudates through center portion 52 to the wearer's clothing or surroundings. In addition, one or both of the layers in center portion 52 may be modified as described above, for example, by hydrophobic treatments.

In some embodiments, it may be desirable to provide greater extension under tension in center portion 52 than in the front portion 54 and/or rear portion 50. This could, for example, allow center portion 52 to expand so as not to mechanically constrain the absorption of exudates into absorbent insert 14, and limit the extension of front portion 54 and/or rear portion 50 to provide better unload forces for sustained fit around the wearer's waist and hips.

In some embodiments, one or more portion of outer cover 12 may have three or more layers. For example, in addition to rear portion 50, center portion 52, and front portion 54, outer cover 12 may have a leg portion 60. Leg portion 60 may run more or less parallel to perimeter 38 in center portion 52, and may extend a distance from perimeter 38 which is greater than 0 mm, but less than approximately one-third the width of outer cover 12 at its narrowest point in center portion 52, on each longitudinally-extending lateral side 62 of outer cover 12. If perimeter 38 is curvilinear in center portion 52, leg portion 60 may have generally the same curvature as perimeter 38. Outer cover 12 may comprise three or more layers in rear portion 50. Leg portion 60, if present, may comprise three or more layers of material, to provide some stiffness and help hold leg portion 60 against the wearer's body to contain exudates. In some embodiments, rear portion 50 may comprise two layers of fabric and an anchoring band, which may be a different fabric or an elastic band having greater unload forces than the other layers of fabric. In other embodiments, landing zone 24 may comprise three or more layers to provide some stiffness to landing zone 24, which may make it easier to press and attach fasteners 22 to landing zone 24.

One or more portions of outer cover 12 may comprise alternating numbers of layers, longitudinally or laterally or both, to distribute forces within outer cover 12 or provide an appearance of three-dimensionality.

In some embodiments, outer cover 12 comprises two layers in leg portion 60 and one layer in center portion 52, to enhance resistance to gapping at the legs and allow absorbent insert 14 to swell in center portion 52. It should be understood that if center portion 52 differs from leg portion 60, center portion 52 will itself vary laterally, since leg portion 60 is a sub-portion of center portion 52.

In some embodiments, outer cover 12 comprises a central portion 64 of rear waistband 16 and/or front waistband 18 which has different layers than ear portions 62 of rear waistband 16 and/or front waistband 18. Central portion 64 may have a lateral width roughly corresponding to one-third the width of outer cover 12 along laterally-extending longitudinal edge 56 or 58. If laterally-extending longitudinal edge 56 or 58 is rounded or otherwise has no distinct edge, central portion 64 is considered that portion of the waistband corresponding to the width of outer cover 12 at the laterally narrowest point of longitudinal central portion 52. Ear portions 62 are those portions of the outer cover along laterally-extending longitudinal edge 56 or 58 which are laterally outboard of lateral central portion 64. Ear portions 62 and lateral central portion 64 may extend longitudinally from longitudinal end edge 56 along all of rear portion 50 or from longitudinal end edge 58 along all of front portion 54. Ear portions 62 may comprise fewer layers than lateral central portion 64. For example, ear portions 62 may comprise a single layer of material, and lateral central portion 64 may comprise two layers. Such a construction may allow ear portions 62 to stretch easily, thereby facilitating application of the product to a wearer, while central portion 64 may provide higher unload forces, thereby improving the sustained fit of the product over time.

Of course, it should be understood that the front portion 54 and rear portion 50 may be, but need not be, of like construction with regard to the materials, treatment of the materials, or layers of materials used. Although different constructions are described herein as various embodiments, combinations and permutations of the different constructions are expressly contemplated.

EXAMPLES

| Property | Example 1 | Example 2 | Example 3 | Example 4 | Example 5 |
|---|---|---|---|---|---|
| Strikethrough (s) for all layers of Outer Cover using regular 0.9% saline | 8.86 | 49.0 | 17.8 | 198 | 204 |
| Surface Energy (mJ/mm$^2$) | | | | | |
| polar | 0.89 | 0.87 | 4.71 | 0.092 | 0.47 |
| Non-polar | 1.47 | 3.96 | 26.9 | 27.2 | 28.9 |
| DAT contact angle (degrees)* | | | | | |
| 0.5 sec | 66.5 | 92.5 | 126.9 | 97.7 | 96.7 |
| 1 sec | 25.9 | 85.5 | 126.9 | 97.5 | 96.4 |
| Absorbent capacity (g) | | | | | |
| OC or insert (g) | 44.4 | 28.1 | 18.2 | 37.3 | 24.0 |
| Unitized Capacity (g/g) | | | | | |
| whole OC | 0.63 | 0.46 | 0.30 | 0.70 | 0.72 |
| OC Material only | 1.13 | 1.48 | 0.30 | 0.52 | 0.70 |
| Mass of whole OC (g) | 70.5 | 61.1 | 60.6 | 53.3 | 33.3 |
| Bending stiffness peak force** (Newtons) | 0.183 | 0.355 | 0.381 | 0.261 | 0.206 |

*Measured on the wearer-facing surface of the wearer-facing layer of the outer cover.
**For each type of outer cover, ten samples were tested, using all layers of the Outer Cover (OC), and the average was reported. The outer cover bending stiffness peak force was measured using the Bending Stiffness Test, disclosed herein. Also, for the Test Article, the bending stiffness peak force of the outer layer material was measured using the Bending Stiffness Test, and was found to be 0.070 Newtons. Further, for the Test Article, the bending stiffness peak force of the inner liner material was measured using the Bending Stiffness Test, and was found to be 0.056 Newtons.

Example 1 is an outer cover configured according to embodiments of the present disclosure, with an outer layer material and inner liner material both made of 93% Modal and 7% Spandex, available as code E.n.n-14 from Koshtex, Los Angeles, Calif., United States, outer cover hooks made of 100% nylon, available as sewable hooks from Perfectek Plus, Huntington Beach, Calif., United States, outer cover landing zone, available as code 960E from Aplix, Paris, France, and insert landing zone made of 100% nylon, available as standard sew on material from Touchtape, St. Augustine, Fla., United States.

Example 2 is a gDiaper™ reusable diaper cover purchased from www.gdiapers.com in April 2010. The SKU number is 31041 and the size is Large (26-36 pounds). The manufacturer is gDiapers, Inc. of Portland, Oreg.

Example 3 is a Gro Baby™ reusable diaper cover purchased from www.thenaturalbabyco.com in April 2010. The outer cover is only available in one size. The manufacturer is GroVia™ (formerly Gro Baby™), of Bozeman, Mont.

Example 4 is a Bummis™ SuperBrite reusable diaper cover, size L, purchased from www.thenaturalbabyco.com in April 2010, and manufactured by Bummis, Inc., Montreal, Quebec, Canada.

Example 5 is a Diaperaps™ reusable diaper cover, size large, purchased from www.babysorganicnursery.com in April 2010, manufactured by Diaperaps: Baby's Organic Nursery, Granada Hills, Calif.

Modified Liquid Strike-Though

Liquid strike-through of the outer cover is measured using a Lister Strike Through instrument (available from Lenzing Technik, Austria), or any apparatus compliant with the Harmonized Test Method WSP 70.3 (08). The instrument is calibrated and operated in accordance with the manufacturer's instructions except where specified below. The test fluid was 0.9% w/v sodium chloride prepared in distilled water.

Precondition samples at 23° C.±2° C. and 50%±2% relative humidity for 2 hours prior to testing. The outer cover article is opened and placed with the wearer-facing surface facing downward. Using scissors, remove the leg elastics, if present, such that the article can be laid flat. Select a sampling site along the longitudinal axis of the cover that is equal-distant between the distal edge of the back waist and the midpoint of the cover's total length. If structures such as seams, snaps, labels, etc. are present at this site, it is permissible to shift the sampling region to an adjacent area to avoid them. With a hydraulic press and cutting die (100 mm square±0.1 mm and 8 mm deep), cut a specimen centered on this mark through all the layers of the article, with the specimen's cut edges parallel and perpendicular to the longitudinal and lateral axis of the article. The specimen can be tested with all layers as one composite or as individual layers.

The specimen is placed under the strike-through plate with the wearer-facing surface facing upward, and its edges parallel and perpendicular to the plate (for this experiment no absorbent paper is placed under the specimen). The plate is aligned underneath the delivery funnel such that the funnel is centered over the plate's cavity and is 30 mm±1 mm above the top of the plate's surface. Add 5.00 mL±0.01 mL of the test fluid into the funnel, and then open the valve to deliver the flow into the plate cavity. The test fluid will complete the electrical circuit of the plate electrodes and start the timer. The timer will stop when the liquid has penetrated into the specimen. Record the strike-through time to the nearest 0.01 second.

Repeat the analysis on three equivalent specimens from separate outer covers. Average the three values and report to the nearest 0.01 sec.

Surface Energy

The surface energy of a surface is derived from contact angle measurements, which can be converted to surface energy by various accepted models that would be known to one of skill in the art. One such model, used in the present disclosure, is the Fowkes equation, as described in Fowkes, F. M.: *Industrial and Engineering Chemistry*, vol. 56, number 12, p. 40 (1964) which is herein incorporated by reference:

$$\gamma_{lv}(1+\cos\theta) = 2(\gamma_{lv}{}^d \gamma_{sv}{}^d)^{1/2} + 2(\gamma_{lv}{}^p \gamma_{sv}{}^p)^{1/2}$$

where:
 $\theta$ the contact angle;
 $\gamma_{lv}$ the surface tension of the liquid;
 $\gamma_{lv}{}^d$ the dispersive component of the surface tension of the liquid being deposited on the specimen's surface;
 $\gamma_{sv}{}^d$ the dispersive component of the surface energy of the specimen's surface;
 $\gamma_{lv}{}^p$ the polar component of the surface tension of the liquid being deposited on the specimen's surface;
 $\gamma_{sv}{}^p$ the polar component of the surface energy of the specimen's surface;

Sessile drop contact angle is measured using a FTA 200 dynamic contact angle analyzer with FTA 200 software, version 2.1, build 340 (available from First Ten Angstroms, Portsmouth, Va.), or equivalent. Purified distilled water, processed through a Milli-Q water system (Millipore Corporation, Billerica, Mass.) and 99% diiodomethane (Sigma-Aldrich, Saint Louis, Mo.) are used as the test fluids. All measurements were performed at constant temperature (25° C.±1° C.) and humidity (33%±2%).

Precondition samples at 25° C.±1° C. and 33%±2% relative humidity for 2 hours prior to testing. The outer cover article is opened and placed with the wearer-facing surface facing upward. Using scissors, remove the leg elastics, if present, such that the article can be laid flat. Select a sampling site along the longitudinal axis of the cover that is equal-distant between the distal edge of the back waist and the midpoint of the cover's total length. If structures such as seams, snaps, labels, etc. are present at this site, it is permissible to shift the sampling region to an adjacent area to avoid them. Using scissors excise a 1 cm by 3 cm specimen of the wearer-facing surface from the selected site. The specimen is adhesively mounted flat on a glass microscope slide such that no ridges are present and with the wearer-facing surface facing upward.

Using the FTA 200, 7 μL of purified water is dangled from the end of a blunt tip, 27 gauge stainless steel needle. The surface of the specimen is slowly raised until it makes contact with the drop. A video stream collected at a rate of 120 images/s is optically triggered at first contact between drop and specimen and collects images for the first 1 minute while the drop detaches and subsequently equilibrates with the surface of the specimen. Preferably, the contact angle is measured at 0.2 seconds after drop contact with the specimen surface. If significant penetration of the placed test fluid occurs within that 0.2 seconds, i.e., greater than 2.5%, contact angle is alternatively determined at 0.02 seconds. Contact angle is measured using a non-spherical tracing of the drop profile as automatically determined by the FTA 200 software and reported to the nearest 0.01 degrees.

The above procedure is next repeated using 3 μL of diiodomethane in place of the purified water. Contact angle using diiodomethane is reported to the nearest 0.01 degrees.

The surface energy of the baby-facing surface of the specimen is calculated using the Fowkes equation with the constants listed in Table 1 and recorded to the nearest 0.001 mJ/m$^2$.

TABLE 1

Solvents used to determine surface energy of outer wrap

| Solvent | Surface Energy Component (mJ/m$^2$) | | |
|---|---|---|---|
| | Nonpolar | Polar | Total |
| Water | 21.8 | 51.0 | 72.8 |
| Diiodomethane | 50.8 | 0 | 50.8 |

Dynamic Absorption Test

The Dynamic Absorption Test measures the absorption of a test fluid on to a specimen's surface by measuring the change in contact angle of the test fluid as it makes contact with, and absorbs into the surface. Sessile drop contact angle is measured using a FTA 200 dynamic contact angle analyzer with FTA 200 software, version 2.1, build 340 (available from First Ten Angstroms, Portsmouth, Va.), or equivalent. All measurements are performed at constant temperature (28° C.±1° C.) and humidity (33%±2%). For these experiments, the test fluid was 0.9% w/v sodium chloride (99.9% purity) prepared in purified distilled water, processed through a Milli-Q water system (Millipore Corporation, Billerica, Mass.).

Precondition samples at 28° C.±1° C. and 33%±2% relative humidity for 2 hours prior to testing. The outer cover article is opened and placed with the wearer-facing surface facing upward. Using scissors, remove the leg elastics, if present, such that the article can be laid flat. Select a sampling site along the longitudinal axis of the cover that is equal-distant between the distal edge of the back waist and the midpoint of the cover's total length. If structures such as seams, snaps, labels, etc. are present at this site, it is permissible to shift the sampling region to an adjacent area to avoid them. Using scissors, excise a 1 cm by 3 cm specimen of the wearer-facing surface from the selected site. The specimen is adhesively mounted flat on a glass microscope slide such that no ridges are present and with the wearer-facing surface facing upward.

Using the FTA 200, 7 μL test fluid is dangled from the end of a blunt tip, 27 gauge stainless steel needle. The surface of the specimen is slowly raised until it makes contact with the drop. A video stream collected at a rate of 1 image/0.1 second is optically triggered at first contact between drop and specimen and collects images for the first 3 seconds while the drop detaches and subsequently equilibrates with the surface of the specimen. Contact angle is measured on each image using a non-spherical tracing of the drop profile as automatically determined by the FTA 200 software and reported to the nearest 0.01 degrees.

Centrifuge Retention Capacity (CRC) Test

The Centrifuge Retention Capacity (CRC) is a measure of the fluid retention capacity (absorbent capacity) of a specimen submerged in 0.9% NaCl saline solution for 30 minutes and then subjected to centrifugation. The test is a based on the Worldwide Strategic Partners Standard Test Method WSP 241.2 (09), Gravimetric Determination of Fluid Retention Capacity in Saline Solution after Centrifugation.

For analysis, specimens are placed into a bag constructed from heat-sealable, water-permeable, non-apertured nonwoven material. Specifications for the bag material are given in WSP 241.2 (09). Measure the length (L) and width (W) of the specimen to be tested. Cut a piece of the bag material that is 2×L+50 mm by W+25 mm. Fold the bag material in half across its width and heat-seal two of the open edges approximately 3 to 5 mm from the edges. The finished bag is L+25 mm by W+25 mm. In addition to the bags for samples, prepare three bags of the same dimensions to be used as blanks.

Outer Cover Material Sample Preparation:

The outer cover article is opened and placed with the wearer-facing surface facing downward. Using scissors remove the leg elastics, if present, such that the article can be laid flat. Select a sampling site along the longitudinal axis of the cover that is equal-distant between the distal edge of the back waist and the midpoint of the cover's total length. If structures such as seams, snaps, labels, etc. are present at this site, it is permissible to shift the sampling region to an adjacent area to avoid them. With a hydraulic press and cutting die (76.2 mm square±0.1 mm and 8 mm deep), cut a specimen centered on this mark through all the layers of the article, with the specimen's cut edges parallel and perpendicular to the longitudinal and lateral axis of the article. Obtain and record the dry mass of the specimen to the nearest 0.001 grams. Place all layers of the specimen into an appropriately sized bag and heat seal the remaining open edge. Prepare three replicates of each specimen for testing.

Whole Absorbent Insert Sample Preparation:

Precondition samples at about 23° C.±2° C. and about 50%±2% relative humidity for 2 hours prior to testing. The absorbent insert is unfolded and placed with the wearer-facing surface facing upward. Using scissors cut any elastic along the longitudinal edges of the article at an interval of approximately 2 cm, such that the article can be laid flat. Lay the absorbent insert on a piece of aluminum foil and cut the absorbent insert along the longitudinal and lateral axis resulting in four individual specimens. On a calibrated balance, tare the weight of an appropriately sized bag. Place the specimen, and any material that fell onto the foil during cutting, into the tared bag and heat seal the remaining open edge. Obtain and record the dry mass of the specimen to the nearest 0.001 grams. Repeat this procedure to obtain the dry mass of the three remaining specimens. Three replicate absorbent inserts are prepared for testing.

Whole Outer Cover Sample Preparation:

Obtain and record the dry mass of the entire outer cover to the nearest 0.001 grams. Three replicate outer covers are prepared for testing.

Test Procedure:

Obtain a pan large enough to hold several bags or specimens, and fill it with 0.9% saline solution to a level such that the bag or specimen can be completely submerged. Lay the bags or specimens to be tested onto the surface of the saline, and allow them to become wet for 1 minute before submerging. A weight placed onto the edge of the bag may be used to ensure that the sample remains submerged while allowing the solution to be freely absorbed by the specimen. After 30 minutes remove the bag or specimen from the saline solution, and immediately transfer it into the basket of a suitable centrifuge capable of subjecting the specimens to a 250 G centrifugal acceleration (such as a Clay Adams Dynac Centrifuge available from Block Scientific, Bohemia, N.Y.). Orient the specimens in the centrifuge such that the wearer-facing surface is facing outward, unless the wearer-facing surface is hydrophobic, in which case it should be oriented inward. Position the bags or specimens so that similarly weighted samples are opposite each other for proper balancing. Centrifuge the bags or specimens for 3 minutes±10 seconds at 250 G. The bags or specimens are then removed and immediately weighed. Record the wet mass of the specimen and bag, blank bag, or specimen without a bag to the nearest 0.001 grams.

Calculate the average of the three wet blank bag masses after centrifugation ($m_b$); this value is disregarded if the specimen was tested without a bag. For each specimen (i=1, 2, and 3), calculate the centrifuge retention capacity ($w_i$), expressed as a mass fraction (g/g) using the following equation:

$$w_i = ((m_{wi} - m_b) - m_{si})/m_{si}$$

Where $m_{si}$ is the mass, expressed in grams, of the dry specimen and $m_{wi}$ is the mass, expressed in grams, of the wet specimen and bag or specimen without a bag. For the absorbent inserts cut and tested as four separate specimens. Sum up the four individual masses of the dry specimens to get $m_{si}$, sum up the four individual masses of the wet specimens and bags to get $m_{wi}$, and sum up four of the average wet blank bag masses after centrifugation to get $m_b$. Use these values to calculate a total centrifuge retention capacity ($w_t$) value. Calculate and report the average centrifuge retention capacity for the three replicates to the nearest 0.001 (g/g).

Water Vapor Transmission Rate

Water Vapor Transmission rate (WVTR) is measured according to EDANA/INDA Worldwide Strategic Partners Method WSP 70.4 (08) using a Permatran-W model 100K (MOCON, Minnesota, Minn.). The test method is run as per the WSP standard test, using a test apparatus temperature of 37.8 C, a nitrogen flow rate of 120 SCCM, and the standard mode with 2 cycles and 5 minute exam time. Each cell is individually adjusted to a relative humidity (RH) of 60%±1.5%. The standard reference film (S/N 1008WK089 from MOCON) should be run prior to testing the samples in order to ensure that the equipment is running properly. The standard reference film results should be within ±10% of the values reported by MOCON.

Using scissors or a die cut a specimen 35 mm in diameter. If the outer cover is multilayered the specimen is run as the composite sample. The side of the outer cover which normally faces the skin is oriented toward the water for testing. Report the WVTR as $g/m^2/24$ hr to the nearest 1 $g/m^2/24$ hr.

Coefficient of Friction

The static coefficient of friction can be measured using ASTM Method D 1894-01 with the following particulars. The test is performed on a constant rate of extension tensile tester with computer interface (a suitable instrument is the MTS Alliance using Testworks 4 Software, as available from MTS Systems Corp., Eden Prairie, Minn.) fitted with a coefficient of friction fixture and sled as described in D 1894-01 (a suitable fixture is the Coefficient of Friction Fixture and Sled available from Instron Corp., Canton, Mass.). The apparatus is configured as depicted in FIG. 1c of ASTM 1894-01 using a stainless steel plane with a grind surface of 320 granulation as the target surface. A load cell is selected such that the measured forces are within 10% to 90% of the range of the cell. The tensile tester is programmed for a crosshead speed of 127 mm/min, and a total travel of 130 mm. Data are collected at a rate of 100 Hz.

The test specimen is cut into a square 6.35 cm by 6.35 cm with its sides parallel and perpendicular to the longitudinal axis of the outer cover. The specimen is mounted onto the foam rubber side of the sled using double sided adhesive tape (tape should be wide enough to cover 100% of the sled's surface). The specimen is oriented on the sled such that the skin facing surface of the outer cover will face toward the target surface and the longitudinal axis of the outer cover is parallel to the pull direction of the sled. The mass of the sled with mounted sample is recorded to 0.1 gram. The surface of the stainless steel plane is cleaned with isopropanol between each analysis. To measure the static coefficient of friction against an absorbent insert, the target surface is an 18 gsm matte polypropylene film from Clopay Plastics Products Company of Mason, Ohio.

The Static COF is calculated as follows:

$$\text{Static } COF = A_S/B$$

$A_S$=maximum peak force in grams force (gf) for the initial peak

B=mass of sled in grams

Bending Stiffness Test

Figure 4:
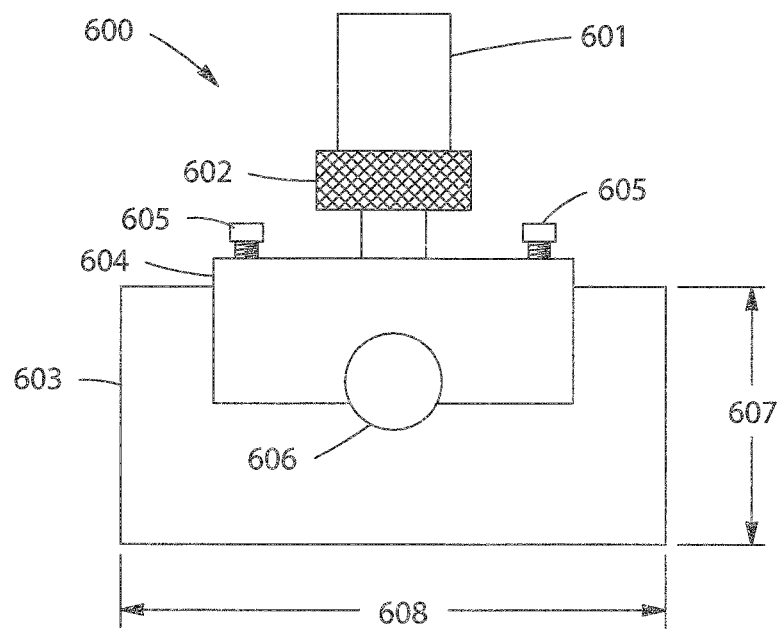
FIG. 4 is a front view of a plunger blade used for the upper movable test fixture in the Bending Stiffness Test.
Figure 5:
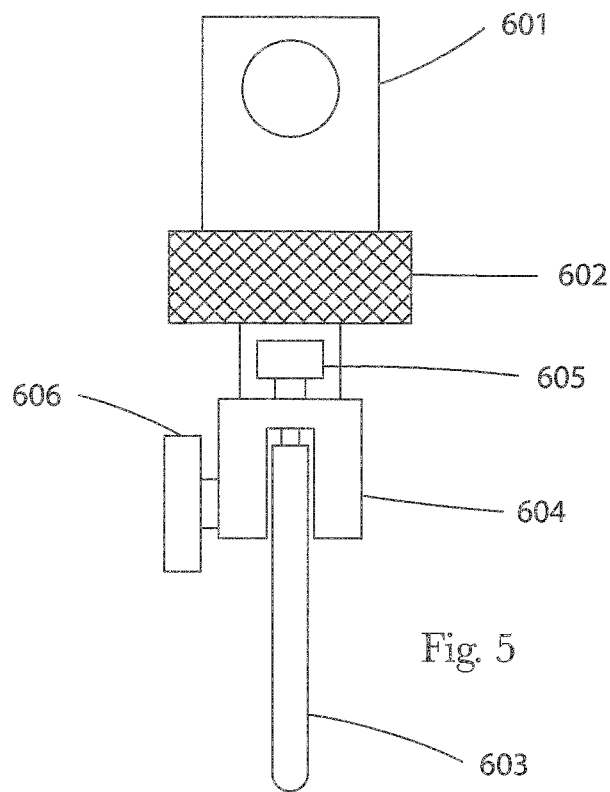
FIG. 5 is a side view of a plunger blade used for the upper movable test fixture in the Bending Stiffness Test.
Figure 6:
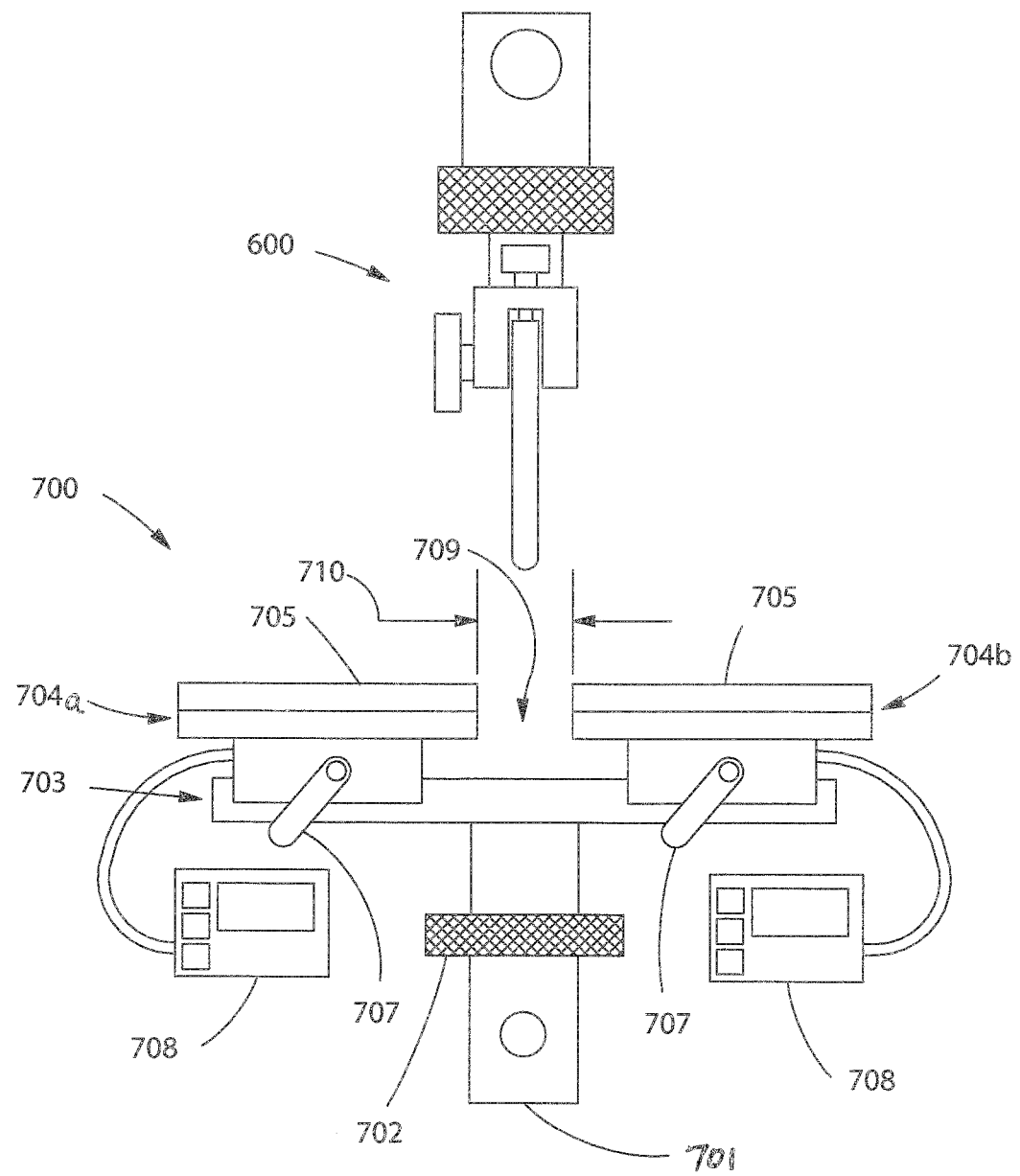
FIG. 6 is a side view of a lower stationary test fixture in the Bending Stiffness Test.

Peak Bending Force and Total Stiffness are measured using a constant rate of extension tensile tester with computer interface (a suitable instrument is an MTS Alliance under TestWorks 4 software, as available from MTS Systems Corp., Eden Prairie, Minn.) using a load cell for which the forces measured are within 10% and 90% of the limit of the cell. A plunger blade 600, shown in FIG. 4 (front view) and FIG. 5 (side view), is used for the upper movable test fixture. Base support platforms 700, shown in FIG. 6, are used as the lower stationary test fixture. All testing is performed in a conditioned room maintained at about 23° C.±2° C. and about 50%±2% relative humidity.

Components of the plunger 600 are made of a light weight material such as aluminum to maximize the available load cell capacity. The shaft 601 is machined to fit the tensile tester and has a locking collar 602 to stabilize the plunger and maintain alignment orthogonal to base support platforms 704. The blade 603, is 115 mm long 608 by 65 mm high 607 by 3.25 mm wide 609, and has a material contact edge with a continuous radius of 1.625 mm. The bracket 604 is fitted with set screws 605 that are used to level the blade and a main set screw 606 to firmly hold it in place after adjustment.

The bottom fixture 700 is attached to the tensile tester with the shaft 701 and locking collar 702. Two horizontally movable support platforms 704 are mounted on a rail 703. Each test surface 705 is 85 mm wide 706 by 115 mm long (into plane of drawing) and made of polished stainless steel so as to have a minimal coefficient of friction. Each platform has a digital position monitor 708 which reads the individual platform positions, and set screws 707 to lock their position after adjustment. The two platforms 704 are square at the gap edge and the plate edges should be parallel front to back. The two platforms form a gap 709 with an adjustable gap width 710.

Accurately (±0.02 mm) align the plunger blade 603 so that it is orthogonal to the top surface of the support platforms 704 and exhibits no skew relative to their gap edges. Using the position monitors 708, accurately set the gap 710 to 13.25±0.02 mm between the two gap edges of the support platforms 704, with the plunger blade 603 accurately (±0.02 mm) centered in the gap. Set the gauge length from the bottom of the plunger blade 603 to the top surface of the support platform 704 to 15 mm. Program the tensile tester to perform a compression test, collecting force and extension data at an acquisition rate of 200 Hz as the crosshead lowers at a rate of 500 mm/min for a total distance of 35 mm.

Precondition samples at about 23° C.±2° C. and about 50%±2% relative humidity for 2 hours prior to testing. The outer cover article is opened and placed with the wearer-facing surface facing downward. Using scissors remove the leg elastics, such that the article can be laid flat. Identify and mark the center of a sampling region which is representative of the material making up the majority of the article, ensuring that it is free of seams, snaps, labels, etc. The sampling region may often be located toward the back/crotch region of the article. With a hydraulic press and cutting die (76.2 mm square±0.1 mm and 8 mm deep), cut a specimen centered on this mark through all the layers of the article, with the specimen's cut edges parallel and perpendicular to the longitudinal and lateral axis of the article.

Place the all layers of the specimen flat onto the surface of the support platform 704 over the gap 709 with the wearer-facing surface facing upward. Arrange the specimen 1009 under the blade 603 such that about ⅓ of the specimen is to the right of the blade and ⅔ to the left. The specimen is placed such that the direction corresponding to the lateral axis of the absorptive article it was harvested from is parallel to the length of the blade. Zero the load cell; start the tensile tester and the data acquisition. Program the software to calculate the maximum Peak Bending Force (N) from the constructed force (N) verses extension (m) curve, and record as "Lateral face-up".

Remove the specimen from the gap 709, keeping the wearer-facing side up. Rotate the specimen 90° clockwise, and arrange the specimen under the blade 603 such that about ⅓ of the specimen is to the right of the blade and ⅔ to the left, exposing a fresh area of the specimen for testing. Zero the load cell; start the tensile tester and the data acquisition. Record the maximum Peak Bending Force (N) as "Longitudinal face-up".

Remove the specimen from the gap 709, keeping the wearer-facing side up. Rotate the specimen 90° counter-clockwise, and turn the specimen over from left to right, so that the wearer-facing surface is facing downward. Arrange the specimen under the blade 603 such that about ⅓ of the specimen is to the right of the blade and ⅔ to the left, exposing a fresh area of the specimen for testing. Zero the load cell; start the tensile tester and the data acquisition. Record the maximum Peak Bending Force (N) as "Lateral face-down".

Remove the specimen from the gap 709, keeping the wearer-facing side down. Rotate the specimen 90° counter-clockwise, and arrange the specimen under the blade 603 such that about ⅓ of the specimen is to the right of the blade and ⅔ to the left, exposing a fresh area of the specimen for testing. Zero the load cell; start the tensile tester and the data acquisition. Record the maximum Peak Bending Force (N) as "Longitudinal face-down".

Calculate the Total Stiffness for a specimen by summing the "Lateral face-up", "Longitudinal face-up", "Lateral face-down" and "Longitudinal face-down" forces. Report the Total Stiffness to the nearest 0.001 N. Repeat the test and record the results for 10 samples. Calculate and report the average Total Stiffness.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A diaper comprising an outer cover, the outer cover comprising:
   a front waistband and a rear waistband opposite the front waistband;
   a landing zone adjacent to the front waistband, wherein the landing zone extends perpendicularly across a longitudinal center line of the outer cover;
   a fastener configured to permanently or releasably join to the landing zone to form a waist opening;
   a first connector disposed on the rear portion of the outer cover;
   a second connector disposed on the front portion of the outer cover, wherein the first connector and the second connector are adapted to releasably join an absorbent insert to the outer cover, and wherein the first connector is different from the second connector to indicate a proper orientation of the absorbent insert;
   a first, wearer-facing layer having a wearer-facing surface; and
   a second, garment-facing layer;
   wherein the outer cover has an absorbent capacity between 5 and 100 g and the wearer-facing surface of the first, wearer-facing layer has a DAT contact angle at 0.5 second of less than about 75 degrees, wherein the first, wearer-facing layer and the second, garment-facing layer are both made of Modal and Spandex, wherein the first, wearer-facing layer and the second, garment-facing layer are joined to at least one of the front waistband and the rear waistband, and wherein each of the first, wearer-facing layer and the second, garment-facing layer have a bending stiffness less than 0.10N.

2. The outer cover of claim 1, wherein the second, garment-facing layer is hydrophobic.

3. The outer cover of claim 1, wherein the outer cover as a whole has a WVTR between 1,200 g/m$^2$/24 hr and 15,000 g/m$^2$/24 hr.

4. The outer cover of claim 3, wherein the outer cover as a whole has a WVTR between 3,000 g/m$^2$/24 hr and 10,000 g/m$^2$/24 hr.

5. The outer cover of claim 1, wherein the wearer-facing surface of the first, wearer-facing layer has a nonpolar component of surface energy of less than about 3.5 mJ/mm$^2$.

6. The outer cover of claim 5, wherein the wearer-facing surface has a nonpolar component of surface energy of less than about 3.0 mJ/mm$^2$.

7. The outer cover of claim 6, wherein the wearer-facing surface has a nonpolar component of surface energy of less than about 2.5 mJ/mm$^2$.

8. The outer cover of claim 1, wherein the wearer-facing surface of the first, wearer-facing layer has a DAT contact angle at 1 second of less than about 70 degrees.

9. The outer cover of claim 8, wherein the wearer-facing surface of the first, wearer-facing layer has a DAT contact angle at 1 second of less than about 45 degrees.

10. The outer cover of claim 1, wherein the first, wearer-facing layer has a strikethrough time of less than about 15 seconds.

11. The outer cover of claim 1, wherein the first, wearer-facing layer has a strikethrough time of less than about 10 seconds.

12. The outer cover of claim 1, wherein the first, wearer-facing layer has a strikethrough time between 1 and 15 seconds.

13. The outer cover of claim 1, further comprising a third layer disposed between the first, wearer-facing layer and the second, garment-facing layer, wherein the third layer is hydrophobic.

14. A diaper comprising an outer cover, the outer cover comprising a single layer or laminate of material, wherein the outer cover comprises:

a first, wearer facing surface;

a second, garment facing surface opposite the first, wearer facing surface;

a front waistband and a rear waistband opposite the front waistband;

a landing zone disposed on the wearer-facing surface of the outer cover, wherein the landing zone extends perpendicularly across a longitudinal center line of the outer cover;

a fastener configured to permanently or releasably join to the landing zone to form a waist opening;

a legband attached to a portion of a perimeter of the outer cover and intermediate the front waistband and the rear waistband;

a first connector adjacent to the front waistband and a second connector adjacent to the rear waistband, wherein the first and second connectors are adapted to permanently or releasably join an absorbent insert to the outer cover, and wherein the first connector has at least one of a different shape and a different dimension than the second connector to indicate a desired orientation of the absorbent insert;

wherein the outer cover has an absorbent capacity between 5 and 100 g and the first, wearer-facing surface has a DAT contact angle at 0.5 second of less than about 75 degrees, wherein the outer cover is made of Modal and Spandex.

15. The outer cover of claim 14, wherein the second, garment-facing surface is hydrophobic.

16. The outer cover of claim 14, wherein the outer cover has a WVTR between 1,200 g/m$^2$/24 hr and 15,000 g/m$^2$/24 hr.

17. The outer cover of claim 16, wherein the outer cover has a WVTR between 3,000 g/m$^2$/24 hr and 10,000 g/m$^2$/24 hr.

18. The outer cover of claim 15, wherein the second, garment-facing surface is coated with a water resistant compound.

19. The outer cover of claim 18, wherein the water resistant compound is selected from the group consisting of polytetrafluoroethylene, fluorocarbon derivatives, hydrophobic silicone polymers, hydrophobic fluorinated polymers, and combinations thereof.

* * * * *